US012796902B2

(12) United States Patent
Kim

(10) Patent No.: US 12,796,902 B2
(45) Date of Patent: Nov. 17, 2026

(54) THERMOMETER WITH ENDOSCOPE AND SYSTEM FOR CHECKING HEALTH THROUGH EAR

(71) Applicant: Otiton Medical Co., Ltd., Seoul (KR)

(72) Inventor: Jae Young Kim, Seoul (KR)

(73) Assignee: Otiton Medical Co., Ltd., Seoul (KR)

( * ) Notice: Subject to any disclaimer, the term of this patent is extended or adjusted under 35 U.S.C. 154(b) by 183 days.

(21) Appl. No.: 18/827,246

(22) Filed: Sep. 6, 2024

(65) Prior Publication Data

US 2025/0213104 A1 Jul. 3, 2025

(30) Foreign Application Priority Data

Dec. 29, 2023 (KR) ........................ 10-2023-0197547

(51) Int. Cl.

| | |
|---|---|
| ***A61B 1/227*** | (2006.01) |
| ***A61B 1/00*** | (2006.01) |
| ***A61B 1/04*** | (2006.01) |
| ***G01K 13/20*** | (2021.01) |

(52) U.S. Cl.

CPC .......... *A61B 1/227* (2013.01); *A61B 1/00016* (2013.01); *A61B 1/0002* (2013.01); *A61B 1/0005* (2013.01); *A61B 1/00066* (2013.01); *A61B 1/00105* (2013.01); *A61B 1/00131* (2013.01); *A61B 1/04* (2013.01); *G01K 13/20* (2021.01)

(58) Field of Classification Search

CPC ............ A61B 1/00096; A61B 1/00097; A61B 1/00101; A61B 1/227; G01K 13/20

See application file for complete search history.

(56) References Cited

U.S. PATENT DOCUMENTS

2002/0193665 A1* 12/2002 Jones ................. A61B 1/00105 600/200
2005/0080354 A1* 4/2005 Crossley ................... G01J 5/02 600/549
2015/0351606 A1* 12/2015 Ruppersberg ........ A61B 5/7275 600/200
2016/0058960 A1* 3/2016 Papania ............ A61M 15/0028 128/200.22

(Continued)

FOREIGN PATENT DOCUMENTS

JP 2004-255029 A 9/2004
JP 2011-520501 A 7/2011

(Continued)

OTHER PUBLICATIONS

"Notice of Reasons for Refusal" Office Action issued in JP 2024-088259; mailed by the Japanese Patent Office on Dec. 3, 2024.

(Continued)

*Primary Examiner* — Julianna N Harvey
*Assistant Examiner* — Steven J Cotroneo
(74) *Attorney, Agent, or Firm* — Studebaker Brackett PLLC

(57) ABSTRACT

A thermometer with an endoscope includes a handle part, a thermometer installed in the handle part, and that measures a body temperature while being inserted into an inner ear, and an endoscope module installed in the handle part, and that photographs the inner ear.

6 Claims, 4 Drawing Sheets

10

(56) References Cited

U.S. PATENT DOCUMENTS

| | | | | |
|---|---|---|---|---|
| 2016/0066797 | A1* | 3/2016 | Lee | A61B 8/14<br>600/301 |
| 2017/0143198 | A1* | 5/2017 | Xiao | A61B 1/07 |
| 2018/0303672 | A1* | 10/2018 | Fan | A61B 1/227 |
| 2018/0353073 | A1* | 12/2018 | Boucher | A61B 5/05 |
| 2020/0113499 | A1* | 4/2020 | Schreiber | A61B 5/0086 |
| 2024/0000397 | A1* | 1/2024 | Merigian | A61B 5/441 |
| 2025/0025033 | A1* | 1/2025 | Perkins | A61B 1/227 |

FOREIGN PATENT DOCUMENTS

| | | | |
|---|---|---|---|
| JP | 2017-514610 | A | 6/2017 |
| KR | 10-2017-0050031 | A | 5/2017 |
| KR | 10-1804374 | B1 | 12/2017 |
| KR | 10-2019-0056005 | A | 5/2019 |

OTHER PUBLICATIONS

Office Action issued in KR 10-2023-0197547; mailed by the Korean Intellectual Property Office on Aug. 6, 2024.

* cited by examiner

THERMOMETER WITH ENDOSCOPE AND SYSTEM FOR CHECKING HEALTH THROUGH EAR

CROSS-REFERENCE TO RELATED APPLICATIONS

A claim for priority under 35 U.S.C. § 119 is made to Korean Patent Application No. 10-2023-0197547 filed on Dec. 29, 2023, in the Korean Intellectual Property Office, the entire contents of which are hereby incorporated by reference.

BACKGROUND

Embodiments of the present disclosure described herein relate to a thermometer with an endoscope and a system for checking health through an ear, and more particularly, relate to a thermometer with an endoscope and a system for checking health through an ear, by which health may be checked by providing an endoscope that provides an image of an inner ear and a thermometer that measure a body temperature in the inner ear.

The thermometer is an electronic thermometer that measures a body temperature, and there are contact types that measure a body temperature while contacting a temperature-sensitive part of the body (an armpit, under the tongue, or the like) and non-contact types that measure heat radiation from an eardrum, or the like.

Then, the non-contact type ear thermometer includes an infrared sensor that is coupled to a probe, and the probe is partially inserted into an ear canal and is aimed toward an eardrum. The device is fundamentally a non-contact type optoelectronic device that measures an intensity of infrared radiation that is emitted from a surface area of the ear canal and converts the infrared signal into an output temperature reading value (see Korean Patent No. 10-1804374).

However, it is difficult to check the health condition of the user by simply measuring the body temperature, and considering this, a device that measures the body temperature through the ear while easily recognizing the condition of the ear, and enables remote diagnosis by using the identified condition is required.

SUMMARY

To solve this problem, a need for a thermometer with an endoscope and a system for checking health through an ear, by which a body temperature may be measured through an ear while a state of the ear is easily recognized and remote diagnosis is enabled by using the identified condition, is emerging.

Embodiments of the present disclosure provide a thermometer with an endoscope and a system for checking health through an ear, by which health may be checked by providing an endoscope that provides an image of an inner ear and a thermometer that measures a body temperature in the inner ear.

The problems that the present disclosure is trying to solve are not limited to the problems mentioned above, and other problems that are not mentioned may be clearly understood by those skilled in the art from the description below.

According to an embodiment, a thermometer with an endoscope includes a handle part, a thermometer installed in the handle part, and that measures a body temperature while being inserted into an inner ear, and an endoscope module installed in the handle part, and that photographs the inner ear.

According to an embodiment, a system for checking health through an ear, the system includes a thermometer with an endoscope and a communication device, the thermometer with an endoscope includes a handle part, a thermometer installed in the handle part, and that measures a body temperature while being inserted into an inner ear, and an endoscope module installed in the handle part, and that photographs the inner ear, and the communication device receives a capture image captured by the endoscope module, and then displays the capture image.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

The present disclosure is not limited to the embodiments disclosed below, but may be implemented in various different forms, and these embodiments are provided only to ensure that the disclosure of the present disclosure is complete and to fully inform a person having ordinary skill in the art, to which the present disclosure belongs, of the scope of the present disclosure.

In the specification, a singular form includes a plural form unless specifically stated otherwise. The terms "comprises" and/or "comprising" used in the specification do not exclude the presence or addition of one or more other elements, stages, and operations mentioned.

Figure 1:
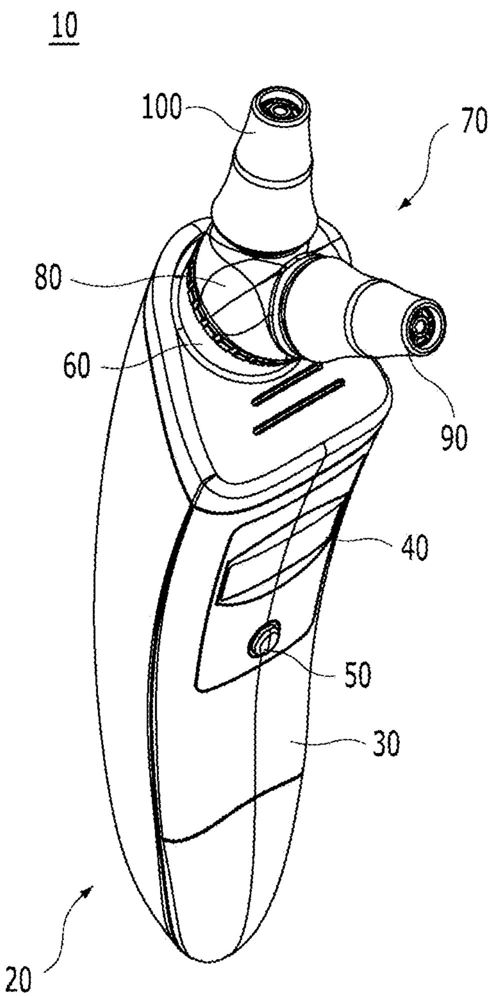
FIG. 1 is a perspective view of a thermometer with an endoscope according to an embodiment of the present disclosure.
Figure 2:
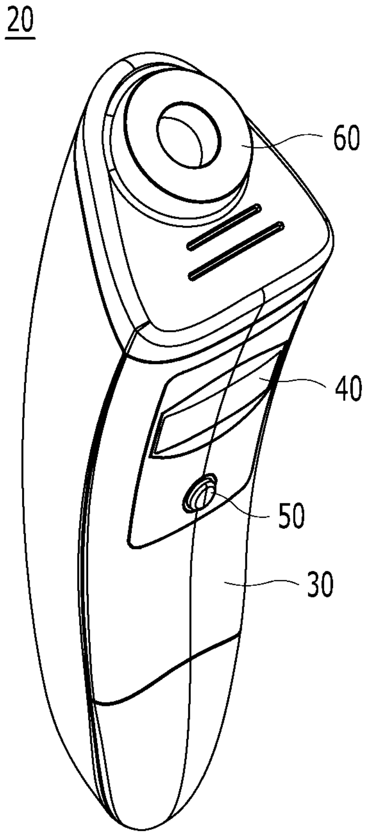
FIG. 2 is a perspective view of a handle part of a thermometer with an endoscope.
Figure 3:
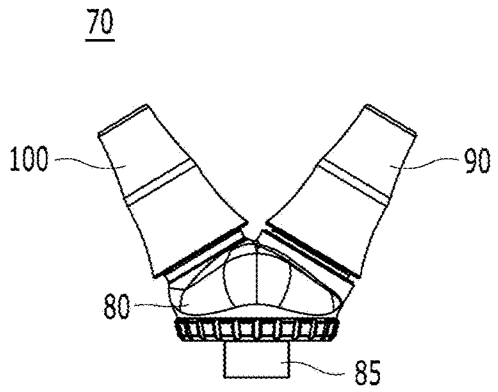
FIG. 3 is a perspective view of a head part of a thermometer with an endoscope.
Figure 4:
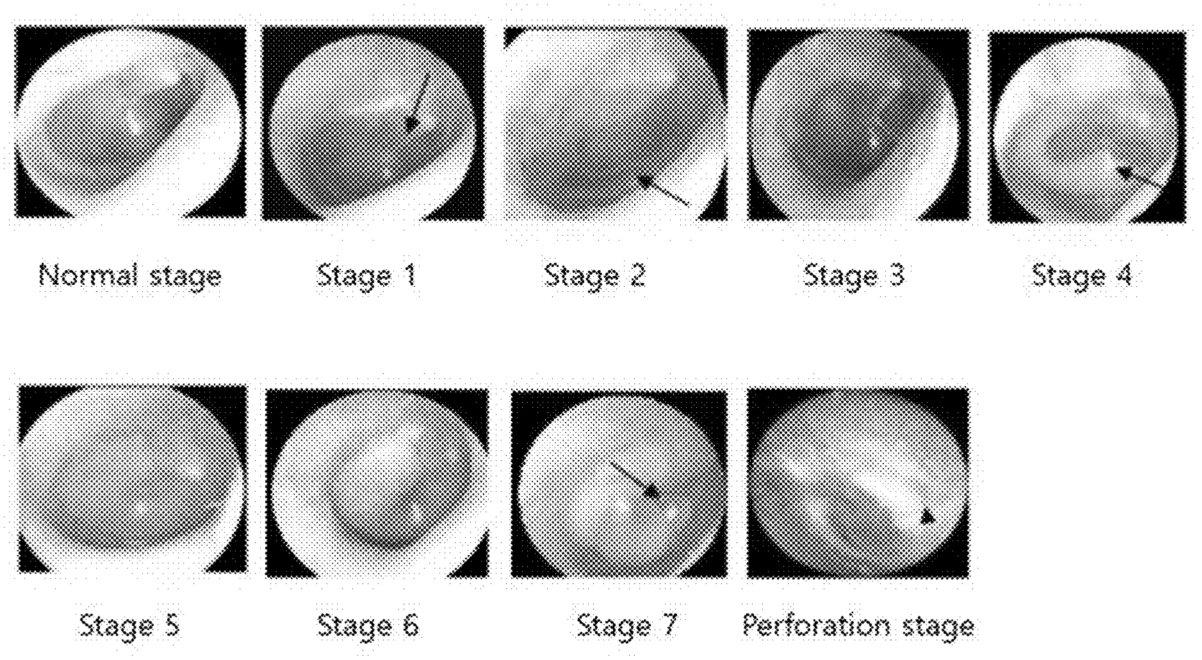
FIG. 4 is a drawing illustrating a progression state of otitis media.

A thermometer with an endoscope according to an embodiment of the present disclosure will be described with reference to FIGS. 1 to 4. FIG. 1 is a perspective view of a thermometer with an endoscope according to an embodiment of the present disclosure. FIG. 2 is a perspective view of a handle part of a thermometer with an endoscope. FIG. 3 is a perspective view of a head part of a thermometer with an endoscope. FIG. 4 is a drawing illustrating a progression state of otitis media.

Referring to FIGS. 1 to 4, a thermometer 10 with an endoscope according to an embodiment of the present disclosure may include a handle part 20 and a head part 70.

The handle part 20 is a part that a user holds with his/her hand to use the thermometer 10 with an endoscope.

The handle part 20 may include a body 30, a display window 40, a button 50, and a coupling part 60.

The body 30 may be a part that a user holds with his/her hand, and may be a configuration, in which the display window 40 and the button 50 are installed.

The display window 40 is a configuration, in which a body temperature of a person measured by a thermometer 90 that will be described below and a state message of the device are displayed.

The button 50 is a configuration that controls an operation of the thermometer 90 and the endoscope, and, when being operated, the thermometer 90 may be operated to measure body temperature, or the endoscope may be operated to photograph an inner ear.

This button 50 may be in the form of a single button or two or more buttons, and in the case of a single button, the operations of the thermometer 90 and the endoscope may be controlled with one button, and in the case of two or more buttons, there may be buttons that are assigned to the thermometer 90 and the endoscope, respectively.

The coupling part 60 is a part, to which the head part 70 that will be described below is coupled to be rotatable.

The handle part 20 may be coupled to the head part 70 through the coupling part 60, and the coupled head part 70 may be rotated on the coupling part 60.

Meanwhile, in FIG. 3, it is illustrated that the coupling part 60 is has a protruding shape, in which a coupling hole is formed at a center thereof, but the coupling part 60 is not limited to the shape.

Next, the head part 70 is a configuration, in which the thermometer 90 and the endoscope module 100 are installed, and which may be coupled to the handle part 20 to be rotatable.

The head part 70 may include a rotation body 80, the thermometer 90, and the endoscope module 100.

The rotation body 80 may be formed to be rotatable with respect to the handle part 20, and in detail, a fitting boss 85 may be formed at a lower portion of the rotation body 80, and the fitting boss 85 may be fitted into a coupling hole of the coupling part 60 whereby the rotation body 80 may be coupled to the handle part 20 to be rotatable.

The thermometer 90 is a device that is installed in the rotation body 80 to measure a body temperature of a person while being inserted into the inner ear.

The body temperature measured in this way may be displayed on the display window 40 of the handle part 20 so that the user may recognize the body temperature.

The endoscope module 100 is a device that is installed in the rotation body 80 to photograph the inner ear.

The endoscope module 100 may include an endoscope for photographing the inner ear, and after the endoscope module 100 is inserted into the inner ear, the endoscope may photograph the inner ear to generate a capture image.

Then, the endoscope module 100 may further include a light source, and the light source provides light so that the endoscope may clearly photograph the inner ear. An LED may be used as this light source.

As described above, the thermometer 90 and the endoscope module 100 may be installed in the rotation body 80, and the rotation body 80 may be installed to be rotatable with respect to the handle part 20. Accordingly, by rotating the rotation body 80, the thermometer 90 and the endoscope module 100 may be rotated, and accordingly, the thermometer 90 and the endoscope module 100 may be used alternately.

That is, because the thermometer 10 with an endoscope according to the present disclosure may measure a body temperature and easily identify a condition of the ear, health checks may be easily performed at any time.

In addition, the thermometer 90 and the endoscope module 100 may be interchangeably coupled to the rotation body 80.

In this case, the thermometer 90 and the endoscope module 100 may be easily managed, and may be replaced with a thermometer and an endoscope module with improved or different functions depending on a situation.

In addition, the thermometer 10 with an endoscope according to the present disclosure may further include a communication module.

The communication module is a module that transmits a capture image of the inner ear, which is taken by the endoscope module 100, to an external device.

In this way, as the communication module transmits the capture image to the external device, the user may easily identify the condition of the inner ear through his or her smartphone, or the like.

Furthermore, the user may photograph a necessary part of the transmitted capture image by using a photo taking function of the smartphone.

In addition, the smartphone that is one of the external devices may store the received capture image, and may store a photo taken from the capture image. Accordingly, the user may track or check a degree of change in the condition of the inner ear through a video and a photo that is stored in the smartphone.

For example, a parent may photograph an inner ear of a child with otitis media by using the thermometer 10 with an endoscope, and the photographed image may be transmitted to and stored in the parent's smartphone.

Accordingly, the parent may identify a change in the condition of the otitis media of the child over time while looking at the captured image stored in the smartphone, and may take appropriate measures.

In detail, as illustrated in FIG. 4, the change in the condition of the inner ear if the child due to the otitis media may progress to a normal stage, stage 1, stage 2, stage 3, stage 4, stage 5, stage 6, stage 7, and a perforation stage, and the parent may recognize the progression state of the otitis media through the capture image and the photo stored in the smartphone.

In addition, the user may transmit these captured images and photos to a hospital 120, or the like to enable remote diagnosis.

Meanwhile, the communication module may be a configuration that is included in the endoscope module 100, or may be a configuration that is installed separately from the endoscope module 100.

Additionally, the communication module may transmit the body temperature measured by the thermometer 90 to an external device, and the external device may store the body temperature information.

Figure 5:
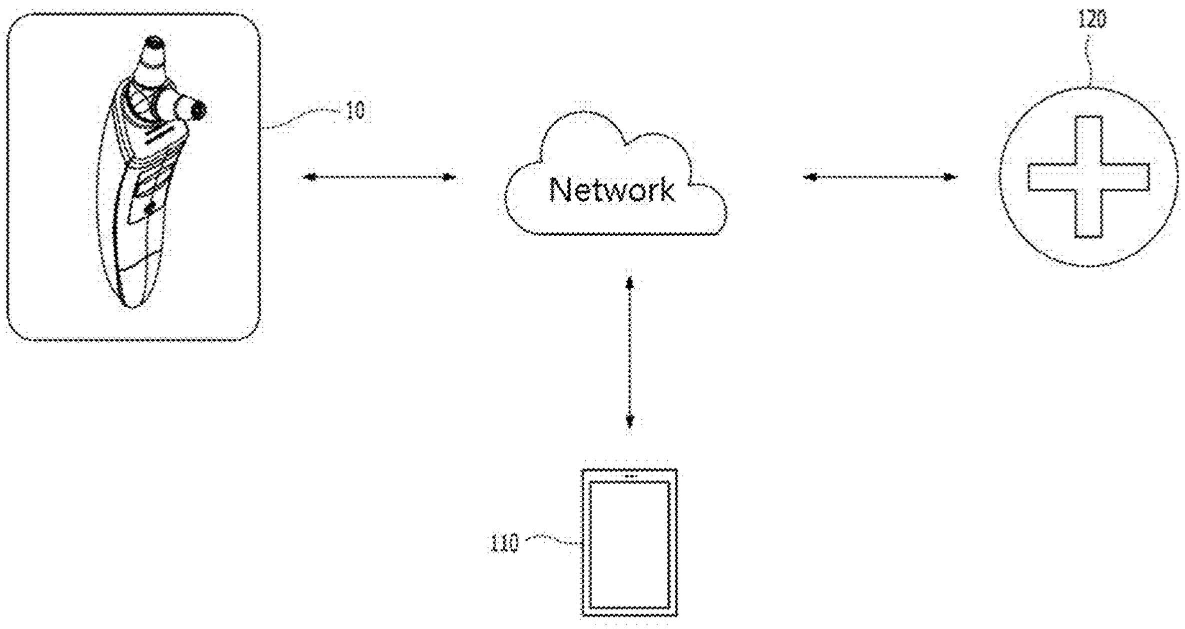
FIG. 5 is a conceptual view of a system for checking health through an ear according to an embodiment of the present disclosure.

Until now, the thermometer with an endoscope according to an embodiment of the present disclosure has been described. Hereinafter, a system for checking health through an ear according to an embodiment of the present disclosure will be described with reference to FIG. 5. FIG. 5 is a conceptual view of a system for checking health through an ear according to an embodiment of the present disclosure.

Referring to FIG. 5, the system for checking health through an ear according to an embodiment of the present disclosure may include the thermometer 10 with an endoscope, a communication device 110, and a hospital 120.

The thermometer 10 with an endoscope may be the same as the thermometer 10 with an endoscope according to an embodiment of the present disclosure described above.

The communication device 110 may receive a capture image captured by the endoscope module 100 and display the received capture image.

The communication device 110 may include a smartphone, and a user who uses the thermometer 10 with an endoscope may receive the capture image through his or her smartphone to easily identify a condition of an inner ear at any time.

Furthermore, the communication device 110 may take a photo from the received capture image by using a photo taking function, and may store the capture image or the photo to show a change in the condition of the inner ear.

As described above, a parent may photograph an inner ear of a child with otitis media by using the thermometer 10 with an endoscope, and the photographed image may be transmitted to and stored in the parent's smartphone.

Accordingly, the parent may identify a change in the condition of the otitis media of the child over time while looking at the captured image stored in the smartphone, and may take appropriate measures.

Referring back to FIG. 4, the change in the condition of the inner ear if the child due to the otitis media may progress to a normal stage, stage 1, stage 2, stage 3, stage 4, stage 5, stage 6, stage 7, and a perforation stage, and the parent may recognize the progression state of the otitis media through the capture image and the photo stored in the smartphone.

Furthermore, the communication device 110 may take a photo from the received capture image by using the photo taking function, and may transmit one or more of the captured images and photos to the hospital 120.

The hospital 120 may recognize the condition of the inner ear of the inner ear after receiving the capture image or the photo of the inner ear, which has been transmitted by the communication device 110. For example, it may recognize whether the user has otitis media, and when so, how severe it is.

The hospital 120 may perform remote treatment, such as transmitting a prescription to the communication device 110 after recognizing the condition of the inner ear of the user, or performing a reservation of an internal examination and transmitting a reservation schedule to the communication device 110.

As discussed above, the thermometer 10 with an endoscope according to the present disclosure may easily recognize the body temperature and the condition of the inner ear of the user, and may transmit the captured image to an external device whereby a remote treatment is enabled.

According to the present disclosure, the thermometer with an endoscope and the system for checking health through an ear, by which a body temperature may be measured through the ear and the inner ear may be photographed at the same time whereby the state of the ear may be easily recognized, and remote diagnosis is enabled by using the captured image.

Although the embodiments of the present disclosure have been described with reference to the attached drawings, those having ordinary skill in the art, to which the present disclosure belongs, will understand that the present disclosure may be implemented in other specific forms without changing the technical idea or essential characteristics thereof. Therefore, the embodiments described above should be understood as being illustrative and not restrictive in all respects.

What is claimed is:

1. A thermometer with an endoscope, comprising:

a handle part comprising a coupling part;

a thermometer installed in the handle part, and configured to measure a body temperature while being inserted into an inner ear;

an endoscope module installed in the handle part, and configured to photograph the inner ear, a rotation body formed to be rotatable about the handle part, and a fitting boss formed at a lower portion of the rotation body, wherein the fitting boss is fitted into a coupling hole of the coupling part, whereby the rotation body is coupled to the handle part to be rotatable, wherein the thermometer and the endoscope module are installed together in the rotation body, and wherein the thermometer and the endoscope module are usable alternately by rotating the rotation body in a state that the thermometer and the endoscope module are not separated from the rotation body.

2. The thermometer of claim 1, wherein the thermometer and the endoscope module are coupled to the rotation body to be exchangeable.

3. The thermometer of claim 1, further comprising:

a communication module configured to transmit a capture image captured by the endoscope module to an external device.

4. A system for checking health through an ear, the system including a thermometer with an endoscope and a communication device, wherein the thermometer with the endoscope includes:

a handle part comprising a coupling part;

a thermometer installed in the handle part, and configured to measure a body temperature while being inserted into an inner ear;

an endoscope module installed in the handle part, and configured to photograph the inner ear, a rotation body formed to be rotatable about the handle part, and a fitting boss formed at a lower portion of the rotation body, wherein the fitting boss is fitted into a coupling hole of the coupling part, whereby the rotation body is coupled to the handle part to be rotatable, wherein the thermometer and the endoscope module are installed together in the rotation body, wherein the thermometer and the endoscope module are usable alternately by rotating the rotation body in a state that the thermometer and the endoscope module are not separated from the rotation body, and wherein the communication device receives a capture image captured by the endoscope module, and then displays the capture image.

5. The system of claim 4, wherein the communication device takes a photo from the capture image by using a photo taking function, and transmits one or more of the capture image and the photo to a hospital.

6. The system of claim 4, wherein the communication device takes a photo from the capture image by using a photo taking function, stores the capture image and the photo, and shows a change in a state of the inner ear.

* * * * *